(12) United States Patent
Kuroda et al.

(10) Patent No.: US 11,076,899 B2
(45) Date of Patent: Aug. 3, 2021

(54) PRESSING TOOL FOR BONE SURGERY

(71) Applicant: OLYMPUS TERUMO BIOMATERIALS CORP., Tokyo (JP)

(72) Inventors: Koichi Kuroda, Kanagawa (JP); Mitsuya Urata, Kanagawa (JP); Ryohei Takeuchi, Kanagawa (JP)

(73) Assignee: OLYMPUS TERUMO BIOMATERIALS CORP., Tokyo (JP)

( * ) Notice: Subject to any disclaimer, the term of this patent is extended or adjusted under 35 U.S.C. 154(b) by 290 days.

(21) Appl. No.: 16/254,669

(22) Filed: Jan. 23, 2019

(65) Prior Publication Data
US 2019/0175235 A1 Jun. 13, 2019

Related U.S. Application Data

(63) Continuation of application No. PCT/JP2017/026224, filed on Jul. 20, 2017.
(Continued)

(51) Int. Cl.
A61B 17/80 (2006.01)
A61B 17/86 (2006.01)

(52) U.S. Cl.
CPC .......... A61B 17/808 (2013.01); A61B 17/80 (2013.01); A61B 17/8004 (2013.01); A61B 17/8685 (2013.01); A61B 17/8033 (2013.01)

(58) Field of Classification Search
CPC ... A61B 17/80; A61B 17/8004; A61B 17/808; A61B 17/8014; A61B 17/8019;
(Continued)

(56) References Cited

U.S. PATENT DOCUMENTS 2,583,896 A 1/1952 Siebrandt
6,579,296 B1 6/2003 Macey
(Continued)

FOREIGN PATENT DOCUMENTS

CN 203970526 U 12/2014
EP 2082698 A2 7/2009
(Continued)

OTHER PUBLICATIONS

International Search Report dated Sep. 19, 2017 issued in PCT/JP2017/026224.
(Continued)

Primary Examiner — Samuel S Hanna
(74) Attorney, Agent, or Firm — Scully, Scott, Murphy & Presser, P.C.

(57) ABSTRACT

A pressing tool for bone surgery according to the present invention includes a pressing member formed substantially columnar shape having, at one end, a pressing surface formed of a convex and substantially spherical surface; and a hook member formed to have a hook shape that is to be engaged with a surface of a bone, the hook member having a support portion at a first end, the support portion supporting the pressing member so that the pressing surface is directed toward a second end, and a projection portion at the second end, the projection portion projecting toward the supporting portion and being to be bited into the surface of the bone, wherein the support portion supports the pressing member in state of the pressing member is movable in a longitudinal direction toward the projection portion.

8 Claims, 13 Drawing Sheets

Related U.S. Application Data

(60) Provisional application No. 62/366,153, filed on Jul. 25, 2016.

(58) Field of Classification Search
CPC ............ A61B 17/7059; A61B 17/6981; A61B 17/8866; A61B 17/1728; A61B 17/746; A61B 17/8061
See application file for complete search history.

(56) References Cited

U.S. PATENT DOCUMENTS

| | | | |
|---|---|---|---|
| 9,370,386 | B2 | 6/2016 | Galm et al. |
| 2002/0183759 | A1 | 12/2002 | Green et al. |
| 2004/0122435 | A1 | 6/2004 | Green et al. |
| 2005/0010226 | A1 | 1/2005 | Grady et al. |
| 2005/0261688 | A1 | 11/2005 | Grady et al. |
| 2009/0216242 | A1 | 8/2009 | Riemer et al. |
| 2010/0274247 | A1 | 10/2010 | Grady et al. |
| 2011/0106183 | A1* | 5/2011 | Dell'oca ............. A61B 17/808 606/86 B |
| 2011/0202093 | A1 | 8/2011 | Grady et al. |
| 2011/0218576 | A1 | 9/2011 | Galm et al. |
| 2013/0296943 | A1 | 11/2013 | Grady et al. |
| 2013/0345762 | A1 | 12/2013 | Dell'Oca et al. |
| 2014/0107652 | A1 | 4/2014 | Walker |
| 2015/0313640 | A1* | 11/2015 | O'Daly ................. A61B 17/17 606/86 R |
| 2016/0175018 | A1 | 6/2016 | Grady et al. |
| 2017/0265880 | A1* | 9/2017 | Kim ...................... A61B 17/17 |
| 2018/0199966 | A1 | 7/2018 | Grady et al. |

FOREIGN PATENT DOCUMENTS

| | | |
|---|---|---|
| EP | 2710968 A1 | 3/2014 |
| JP | 2004-527339 A | 9/2004 |
| JP | 2007-252581 A | 10/2007 |
| JP | 4493618 B2 | 6/2010 |
| JP | 5230697 B2 | 7/2013 |
| JP | 2014-054543 A | 3/2014 |
| WO | WO 99/45856 A1 | 9/1999 |
| WO | WO 02/096294 A2 | 12/2002 |
| WO | WO 2004/107957 A2 | 12/2004 |
| WO | WO 2005/112802 A1 | 12/2005 |
| WO | 2010/014719 A1 | 2/2010 |
| WO | 2011/066280 A1 | 6/2011 |
| WO | WO 2013/191819 A1 | 12/2013 |

OTHER PUBLICATIONS

Takeuchi, R. et al.,"Medial Open Wedge and Lateral Closed Wedge High Tibial Osteotomy that enable Full-Weight-Bearing Walking from Early Postoperative Period", MB Orthopaedics (2013), vol. 26, No. 4, pp. 1-9.

Innomed, Inc., "Product Brochure of Browner MIS Bone Clamp", Retrieved from the Internet, URL:http://www.innomed.net/trauma_clampgrasp.htm.

Synthes, "Small Fragment System. Instruments and implants for 2.7 and 3.5 plate fixation. Technique Guide".

Extended Supplementary European Search Report dated Mar. 5, 2020 in European Patent Application No. 17 83 4142.6.

\* cited by examiner

PRESSING TOOL FOR BONE SURGERY

CROSS-REFERENCE TO RELATED APPLICATIONS

This is a continuation of International Application PCT/JP2017/026224, with an international filing date of Jul. 20, 2017, which is hereby incorporated by reference herein in its entirety. This application claims the benefit of U.S. Patent Application No. 62/366,153, filed on Jul. 25, 2016, the content of which is incorporated herein by reference.

TECHNICAL FIELD

The present invention relates to a pressing tool for bone surgery.

BACKGROUND ART

Osteotomy has been applied to knee osteoarthritis, for example, when the articular cartilage of the patella or the femur is damaged. In osteotomy, after an incision is made in a bone and malalignment of the bone is corrected, the bone is fixed by using a bone joining member, such as a plate, until the bone is healed (for example, refer to Japanese Patent Publication No. 4493618).

Japanese Patent Publication No. 4493618 discloses a bone retainer that can retain both the bone and the bone joining member while the bone joining member is aligned with respect to the bone. According to this bone retainer, screws for fixing the bone joining member to the bone can be driven into the bone via through holes formed in a support portion that supports the bone joining member while the bone and the bone joining member are retained; thus, the task of fixing the bone joining member to the bone can be easily carried out.

SUMMARY OF INVENTION

An aspect of the present invention provides a pressing tool for bone surgery, comprising: a pressurizing member formed substantially columnar shape having, at one end, a pressing surface formed of a convex and substantially spherical surface; and a hook member formed to have a hook shape that is to be engaged with a surface of a bone, the hook member having a support portion at a first end, the support portion is configured to support the pressing member so that the pressing surface is directed toward a second end, and a projection portion at the second end, the projection portion projecting toward the support portion and being to be bited into the surface of the bone, wherein the support portion supports the pressing member in state of the pressing member is movable in a longitudinal direction toward the projection portion.

In the aspect described above, the pressing member may have a male thread and a head portion that is disposed at one end of the male thread and has the pressing surface, and the support portion may have a screw hole to be fastened to the male thread.

In the aspect described above, the projection portion may be positioned on an extended line of an axis line along which the pressing member is movable.

In the aspect described above, the projection portion may be at a position offset from an extended line of an axis line along which the pressing member is movable, in a direction intersecting the extended line.

In the aspect described above, a distance between an extended line of an axis line along which the pressing member is movable and a middle portion of the hook member may be 15 mm or more and 35 mm or less.

In the aspect described above, the projection portion may have one or more pyramid-shaped projections having pointed ends.

In the aspect described above, the hook member may have a slit that allows an interior of the screw hole and an exterior of the support portion to communicate with each other in a radial direction of the screw hole and that extends in a direction along a center axis of the screw hole, wherein a guide pin is inserted into the screw hole in the radial direction.

In the aspect described above, the pressing tool may further include a plug having a receiving portion having a concave receiving surface that is configured to support the pressing surface, and a connecting portion that is configured to connect the receiving portion to a bone joining member that is to be fixed to the surface of the bone.

In the aspect described above, the plug may have a through hole that opens substantially at the center of the receiving surface and allows a guide pin to pass therethrough.

In the aspect described above, the receiving surface of the receiving portion may have a solid angle of 4 steradians or more.

DESCRIPTION OF EMBODIMENTS

In the description below, a pressing tool 1 for bone surgery according to one embodiment of the present invention is described with reference to the drawings.

As illustrated in FIGS. 1A to 1D, the pressing tool 1 for bone surgery according to this embodiment is used in a closed wedge high tibial osteotomy (CWHTO) which involves removing a bone block from the lateral side of the tibia X, closing the bone block excision site Y to correct deformation of the tibia X, and fixing the tibia X with a bone plate (bone joining member) 10. In FIGS. 1A to 1D, an example of a hybrid HTO which combines the closed wedge method and an open wedge method that involves forming an incision in the medial surface of the tibia X and expanding the incision is illustrated.

Figure 1A:
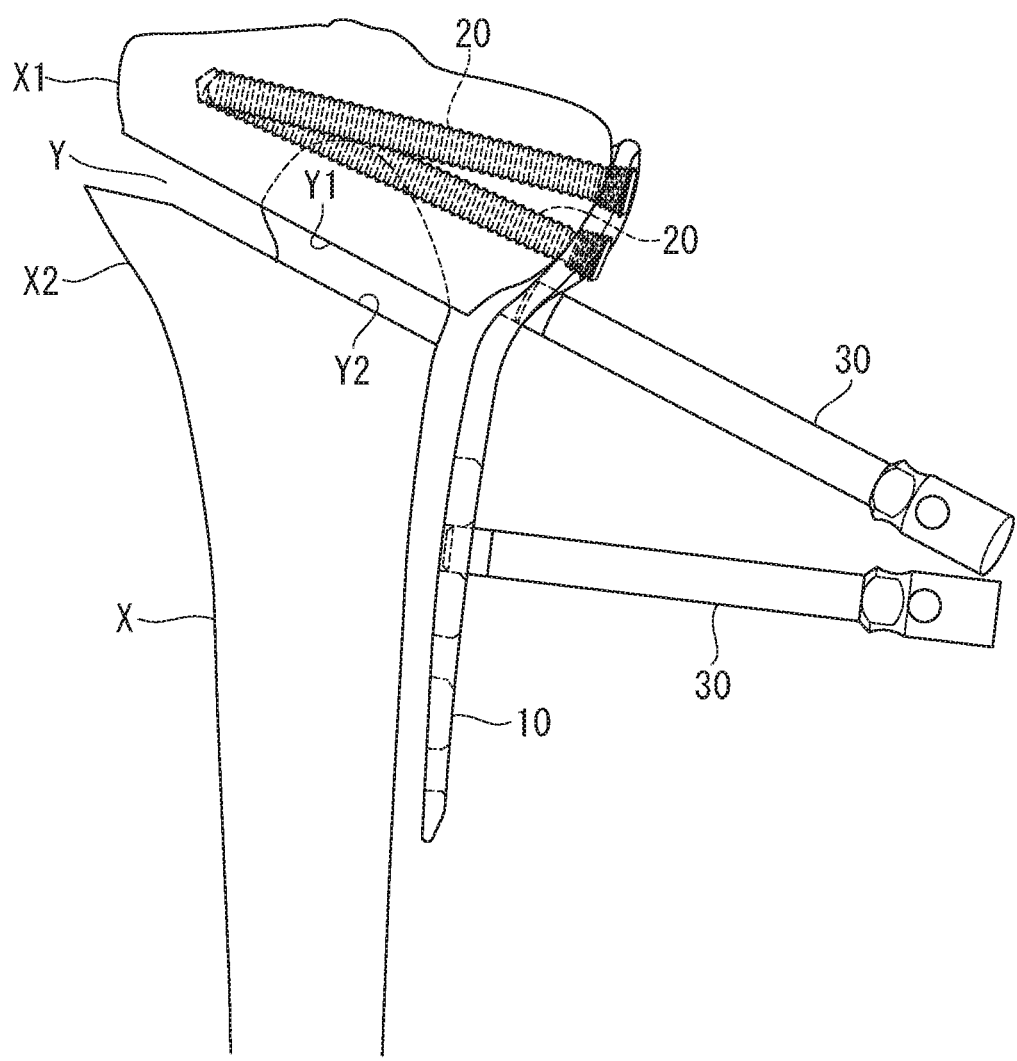
FIG. 1A is a diagram illustrating a high tibial osteotomy that uses a pressing tool for bone surgery according to one embodiment of the present invention.
Figure 1B:
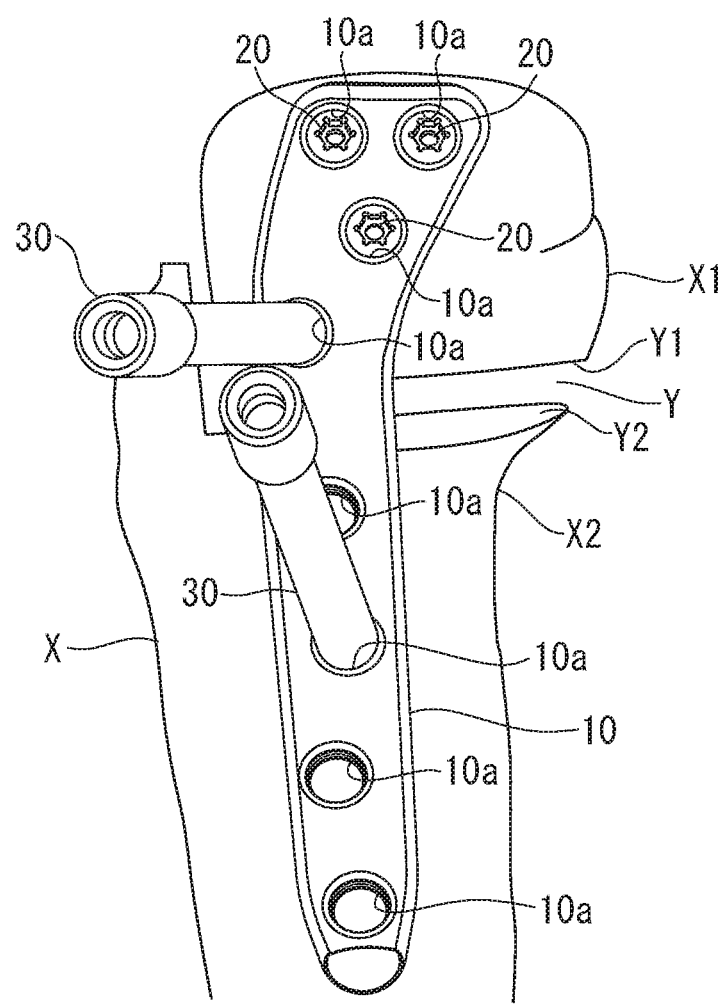
FIG. 1B is a diagram illustrating the tibia illustrated in FIG. 1A as viewed from the bone plate side.

As illustrated in FIG. 1B, the bone plate 10 is a long strip-shaped member placed on a side surface of the tibia X so as to extend in a direction along the longitudinal axis of the tibia X. A plurality of screw holes 10a into which screws 20 for fixing the bone plate 10 to the tibia X are to be inserted are formed in the bone plate 10 so as to be spaced from one another in the longitudinal direction. Reference sign 30 denotes a drill sleeve.

Figure 2:
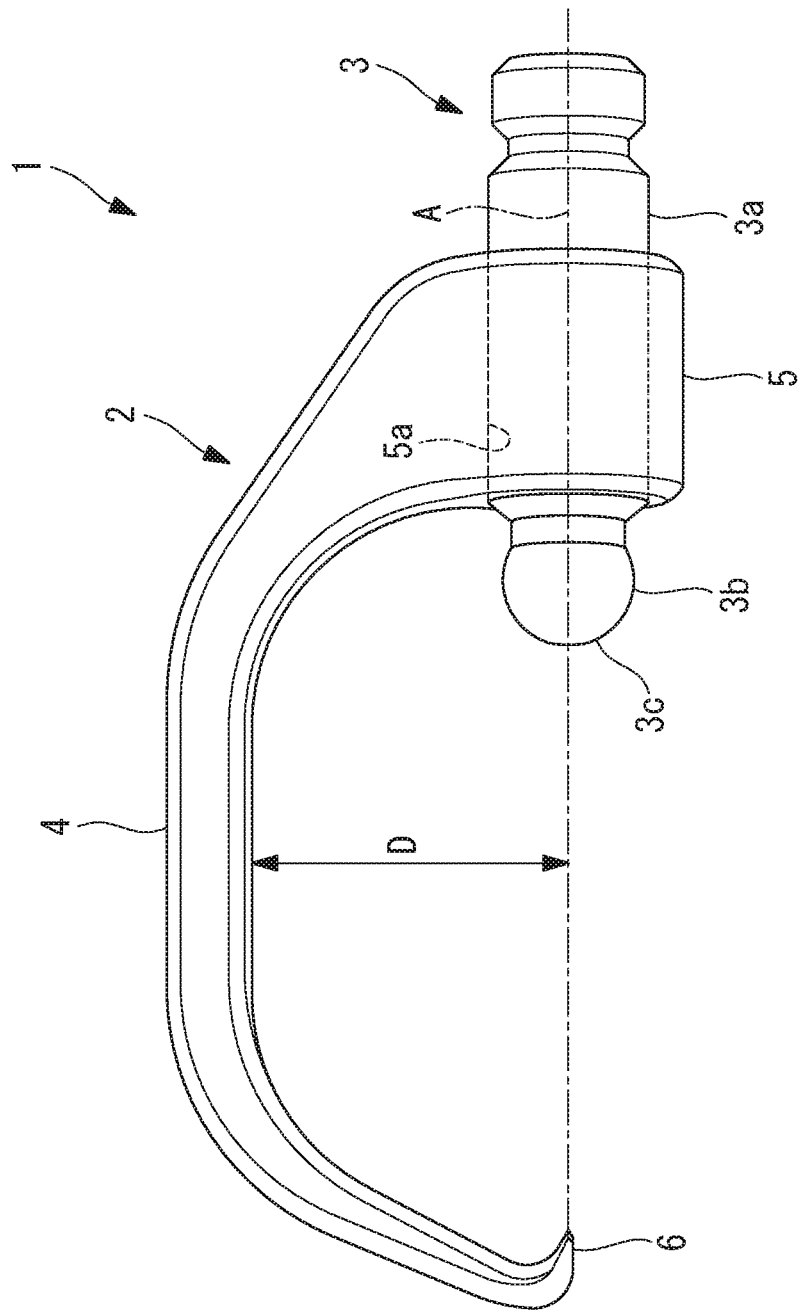
FIG. 2 is a side view illustrating the overall structure of the pressing tool for bone surgery according to one embodiment of the present invention.

As illustrated in FIG. 2, the pressing tool 1 for bone surgery of this embodiment is equipped with a hook member 2 that engages with a side surface of the tibia X, and a pressing screw (pressing member) 3 that presses the bone plate 10 toward the side surface of the tibia X so as to apply a compression force to the tibia X and the bone plate 10. The hook member 2 and the pressing screw 3 are formed of a high-strength metal such as titanium or stainless steel.

The hook member 2 includes a curved portion 4 that is curved to form a shape resembling a hook and that can engage with the side surface of the tibia X; a support portion 5 disposed at a first end of the curved portion 4 to support the pressing screw 3; and a projection portion 6 disposed at a second end of the curved portion 4 and capable of being fixed to the side surface of the tibia X.

The curved portion 4 is formed of a long columnar member and is curved to form a shape resembling a hook so as to cover half around the side surface of the tibia X from the lateral side to the medial side of the tibia X. In a state in which the curved portion 4 is allowed to engage with the side surface of the tibia X along the circumferential direction, the support portion 5 is disposed on the lateral side of the tibia X, and the projection portion 6 is disposed on the medial side of the tibia X.

The support portion 5 has a cylindrical shape having a columnar screw hole 5a that penetrates through in the longitudinal direction and has thread grooves formed in the inner surface. The screw hole 5a extends along a line that connects the first end and the second end of the curved portion 4, and the projection portion 6 is positioned on the extended line of a center axis (axis line) A of the screw hole 5a. The distance D between a middle portion between the first end and the second end of the curved portion 4 and the extended line of the center axis A of the screw hole 5a is preferably 15 mm or more and 35 mm or less so that when the curved portion 4 engages with a thick bone, such as the tibia X or the femur, the pressing screw 3 is positioned so as to be suitable for compressing the lateral surface of the bone.

Figure 3:
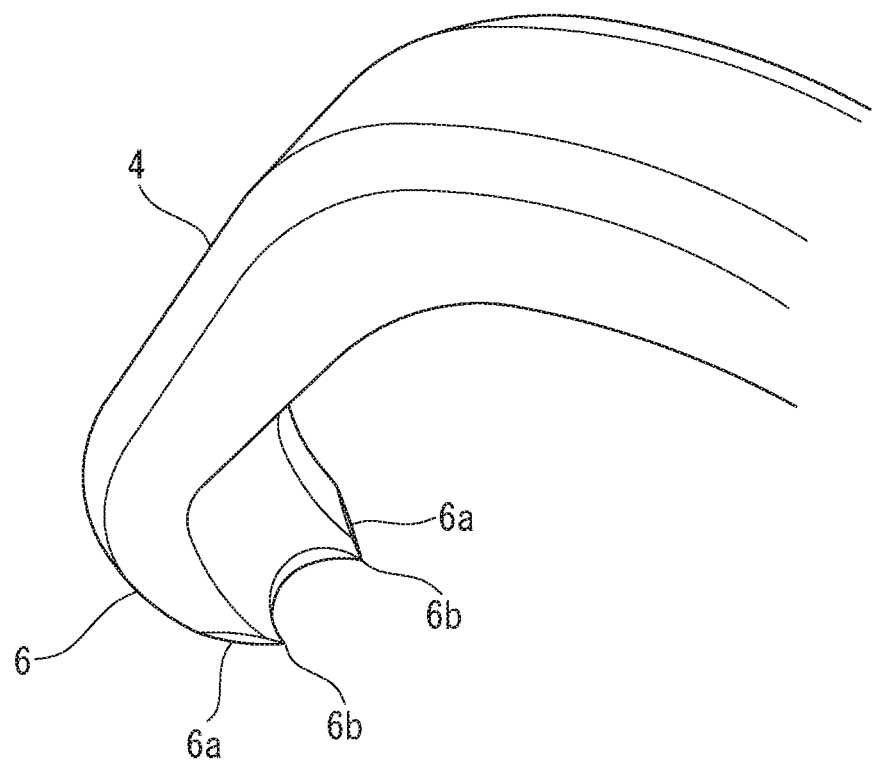
FIG. 3 is a perspective view of a projection portion of a hook member of the pressing tool for bone surgery illustrated in FIG. 2.

The projection portion 6 projects from the second end of the curved portion 4 toward the support portion 5. As illustrated in FIG. 3, a V-shaped groove is formed at the center of the tip of the projection portion 6, and, thus, the tip of the projection portion 6 has two pyramid-shaped projections 6a each having a pointed end 6b. The pointed ends 6b of the projections 6a are caused to bite into the side surface of the tibia X so that the projection portion 6 can be fixed relative to the tibia X.

Figure 4:
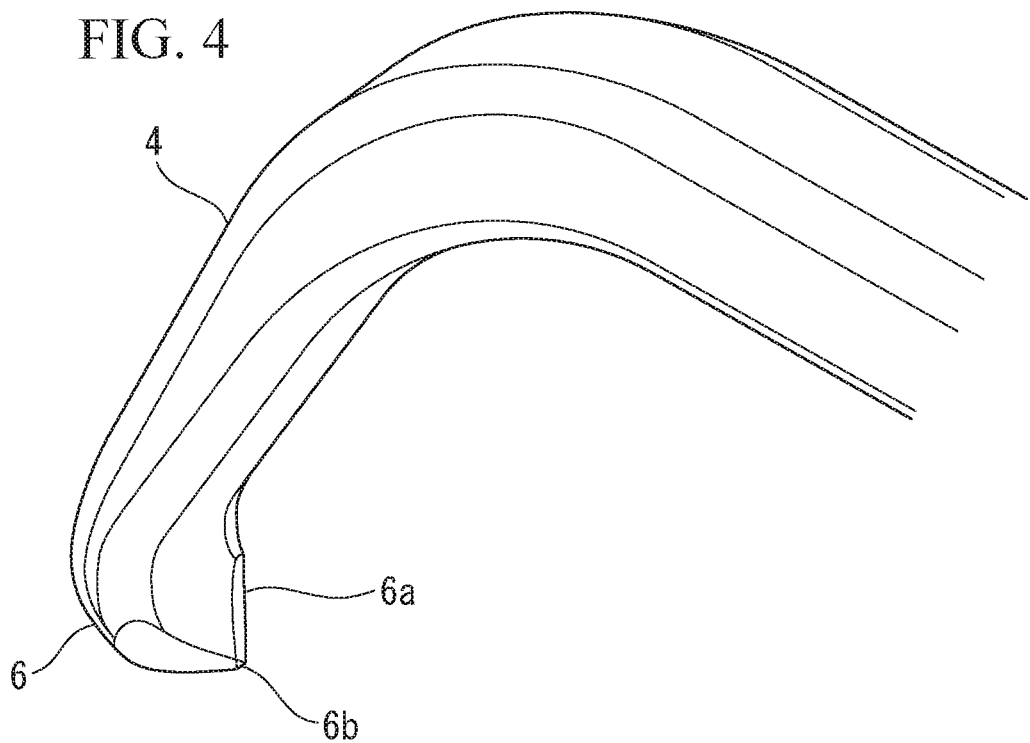
FIG. 4 is a perspective view of a modification of the projection portion of the hook member.
Figure 5:
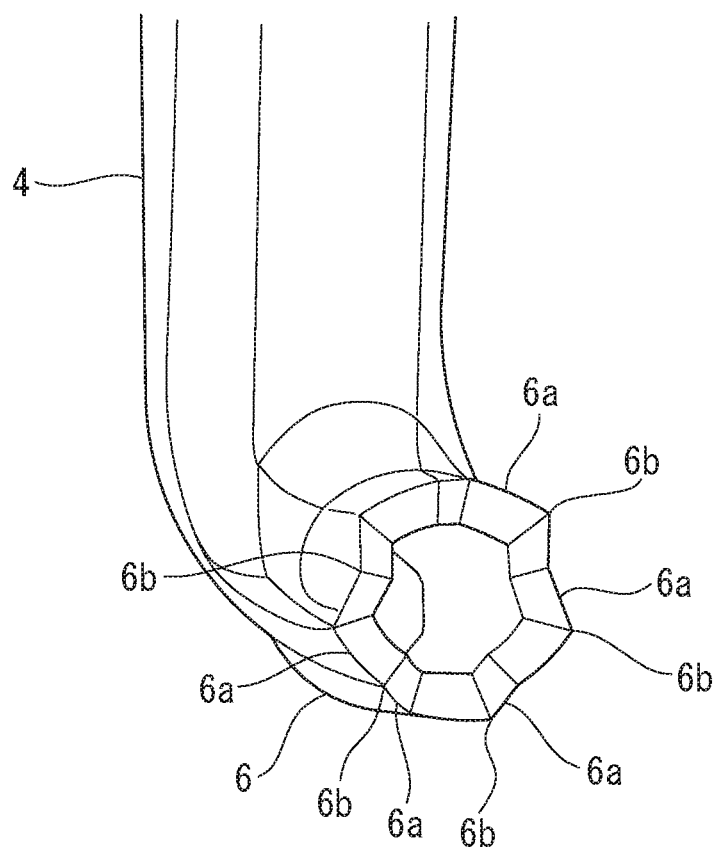
FIG. 5 is a perspective view of another modification of the projection portion of the hook member.

The number of projections 6a formed at the tip of the projection portion 6 is not limited to 2 and may be 1 or 3 or more. For example, as illustrated in FIG. 4, one relatively large projection 6a may be provided, or as illustrated in FIG. 5, three or more circularly arranged projections 6a may be provided.

The pressing screw 3 has a straight, columnar shaft portion 3a and a substantially spherical head portion 3b disposed at one end of the shaft portion 3a. The surface of the head portion 3b opposite to the shaft portion 3a is a pressing surface 3c that applies a pressing force to the bone plate 10 when fitted into a screw hole 10a in the bone plate 10. This surface is formed as a convex and substantially spherical surface.

The shaft portion 3a is a male thread with a screw thread formed in the side surface so that the shaft portion 3a can be fastened to the screw hole 5a in the support portion 5, and is fastened to the screw hole 5a so that the pressing surface 3c of the head portion 3b faces the projection portion 6. As the shaft portion 3a rotates about the center axis thereof, the pressing screw 3 moves along the center axis (axis line) of the screw hole 5a in the longitudinal direction, and the head portion 3b moves along the extended line of the center axis A of the screw hole 5a in a direction toward or away from the projection portion 6.

Next, the effects of the pressing tool 1 for bone surgery having the aforementioned structure are described.

In order to treat knee osteoarthritis by the hybrid HTO technique using the pressing tool 1 for bone surgery of this embodiment, two incisions are formed from the upper lateral surface in the tibia X toward the medial side in directions oblique with respect to the longitudinal axis of the tibia X, and a bone block between two incisions is excised with a particular tool. Next, as illustrated in FIGS. 1A and 1B, the bone plate 10 is placed on the lateral surface of the tibia X so as to bridge the bone block excision site Y, and an upper end portion of the bone plate 10 is fixed with the screws 20 to the tibia X at a position higher than the excision site Y.

Figure 1C:
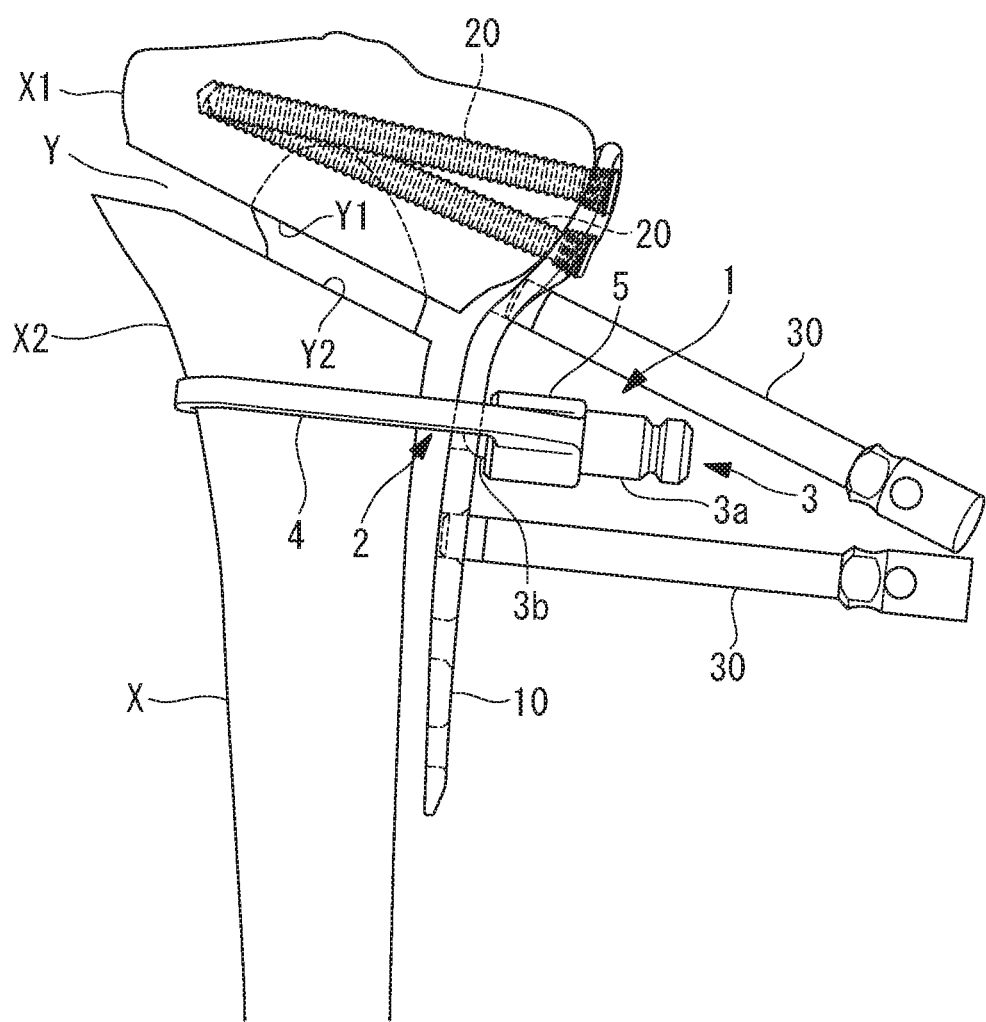
FIG. 1C is a diagram illustrating the high tibial osteotomy that uses the pressing tool for bone surgery according to one embodiment of the present invention.

Next, as illustrated in FIG. 1C, the curved portion 4 of the hook member 2 is allowed to engage with the side surface of the tibia X, and the projection portion 6 is fixed to the medial surface of the tibia X by allowing the pointed ends 6b of the projections 6a to bite into the medial surface of the tibia X. In addition, the support portion 5 supporting the pressing screw 3 is placed so that the bone plate 10 is sandwiched between the lateral surface of the tibia X and the support portion 5.

Next, the pressing surface 3c of the head portion 3b is fitted into the screw hole 10a located on the lower side of the excision site Y, and the shaft portion 3a is rotated to advance the pressing screw 3 toward the bone plate 10. As a result, the distance between the head portion 3b and the projection portion 6 is shortened, and the tibia X and the bone plate 10 sandwiched between the head portion 3b and the projection portion 6 are compressed by the head portion 3b and the projection portion 6 and move close to each other. At this stage, since the projection portion 6 is located on the extended line of the center axis A of the screw hole 5a in which the pressing screw 3 moves, only a compression force working in the center axis A direction of the screw hole 5a, which is the direction in which the pressing screw 3 moves, is applied to the tibia X and the bone plate 10, and the tibia X and the bone plate 10 move only in the center axis A direction.

Figure 1D:
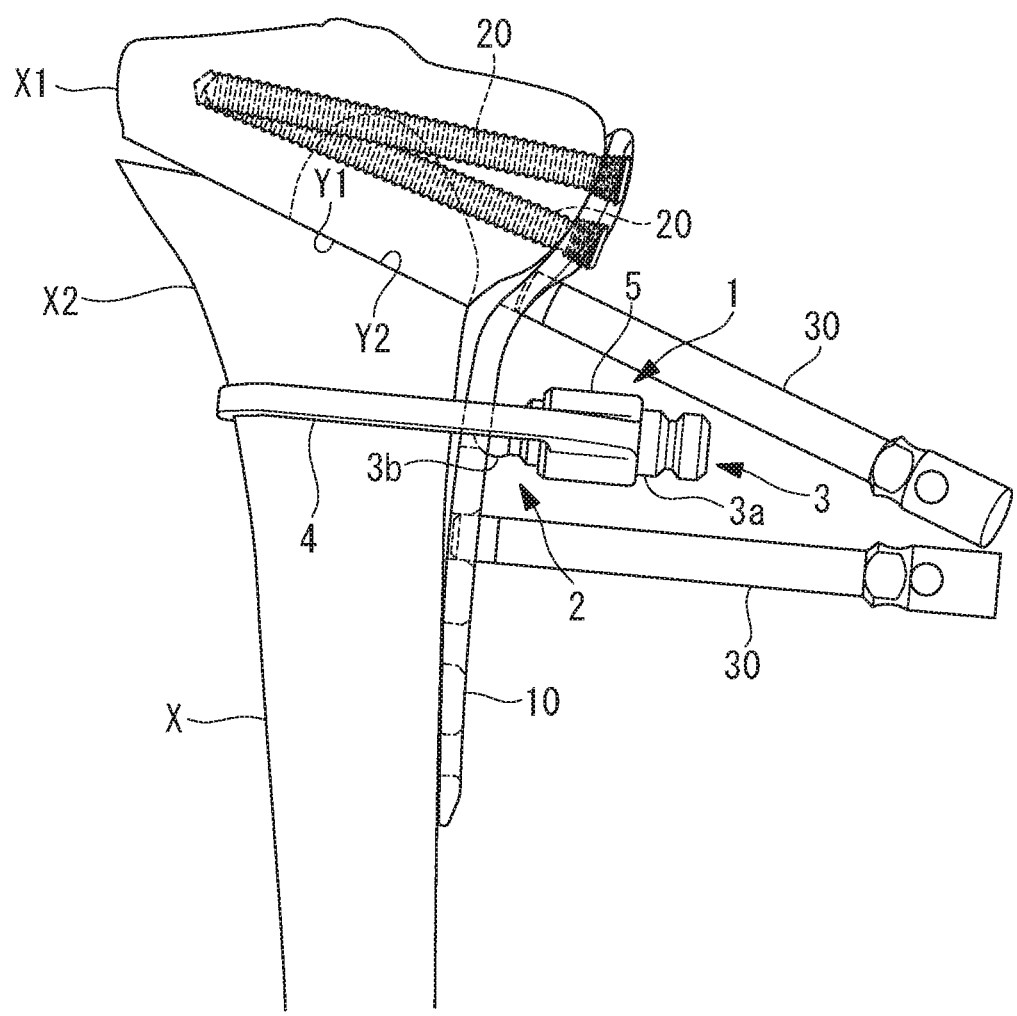
FIG. 1D is a diagram illustrating the high tibial osteotomy that uses the pressing tool for bone surgery according to one embodiment of the present invention.

As illustrated in FIG. 1D, after the shaft portion 3a has been rotated until the bone plate 10 is in close contact with the lateral surface of the tibia X, the screws 20 are inserted into the rest of the screw holes 10a in the bone plate 10 to fix the bone plate 10 to the tibia X.

In this case, when aligning the tibia X and the bone plate 10, as illustrated in FIG. 1D, two portions, X1 and X2, of the tibia X respectively located on the higher side and the lower side of the excision site Y of the tibia X must be aligned so that the two osteotomy surfaces Y1 and Y2 at the excision site Y of the tibia X come into close contact with each other. In other words, a compression force in the longitudinal axis direction must be applied to the tibia X so that the higher portion X1 and the lower portion X2 are drawn toward each other.

Figure 6:
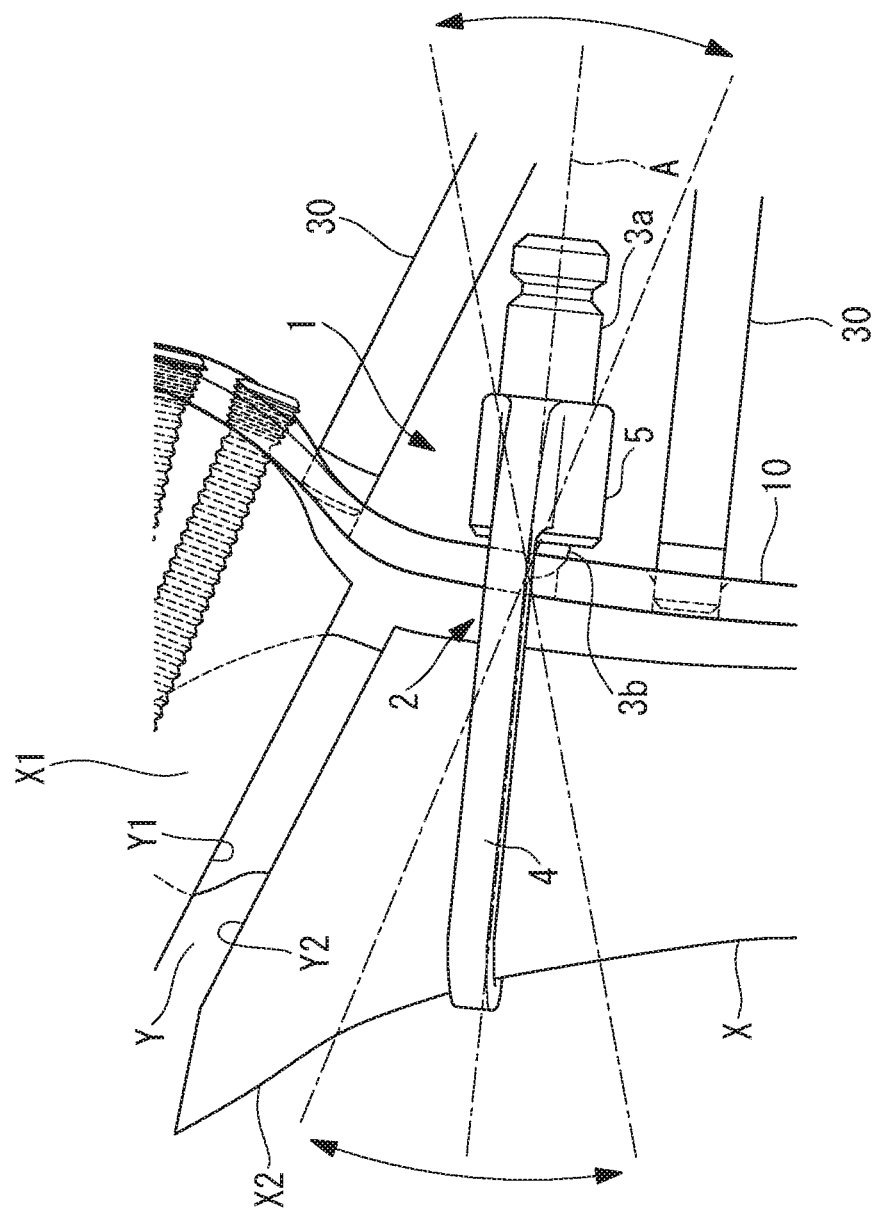
FIG. 6 is a diagram illustrating a method for changing the direction of the compression force applied to the tibia and the bone plate by using the pressing tool for bone surgery illustrated in FIG. 2.

According to this embodiment, as described above, the direction of the compression force applied to the tibia X and the bone plate 10 is coincident with the center axis A direction of the screw hole 5a; thus, as illustrated in FIG. 6, the direction of the compression force can be easily controlled to a desired direction by adjusting the inclination angle of the center axis A of the screw hole 5a with respect to the longitudinal axis of the tibia X.

In other words, by placing the hook member 2 so that the center axis A of the screw hole 5a is inclined with respect to the longitudinal axis of the tibia X, a compression force in a direction oblique to the longitudinal axis of the tibia X is applied to the tibia X and the bone plate 10 so that a compression force in the tibia X radial direction that draws the tibia X and the bone plate 10 close to each other can be generated, and, at the same time, a compression force in the longitudinal axis direction, which is the direction in which the higher portion X1 and the lower portion X2 of the tibia X are drawn toward each other, can be generated. Increasing the inclination angle of the center axis A of the screw hole 5a with respect to the longitudinal axis of the tibia X increases the compression force in the longitudinal axis direction. As such, there is an advantage in that, by applying a compression force in both the direction in which the tibia X and the bone plate 10 are drawn close to each other and the direction in which the osteotomy surfaces Y1 and Y2 are drawn close to each other, the relative position between the three parts, i.e., the higher portion X1 and the lower portion X2 of the tibia X and the bone plate 10, can be adjusted so as to eliminate the gap between the osteotomy surfaces Y1 and Y2.

Moreover, the direction of the compression force can be changed merely by temporarily detaching the pointed ends 6b biting into the tibia X from the tibia X, then shifting the position of the projection portion 6 in the tibia X longitudinal axis direction, and then allowing the pointed ends 6b to again bite into the tibia X. During this process, since the pressing surface 3c of the head portion 3b is spherical, the position of the projection portion 6 can be easily shifted by using the head portion 3b as the supporting point and by rotating the head portion 3b in the screw hole 10a. As such, there is an advantage in that the direction of the compression force applied to the tibia X and the bone plate 10 can be easily changed.

Also, there is an advantage in that if alignment of the higher portion X1 and the lower portion X2 of the tibia X and the bone plate 10 was not successfully carried out in the first attempt, the compressing operation can be easily repeated by rotating the shaft portion 3a in the opposite direction to retract the pressing screw 3 to the side opposite from the bone plate 10.

Figure 7:
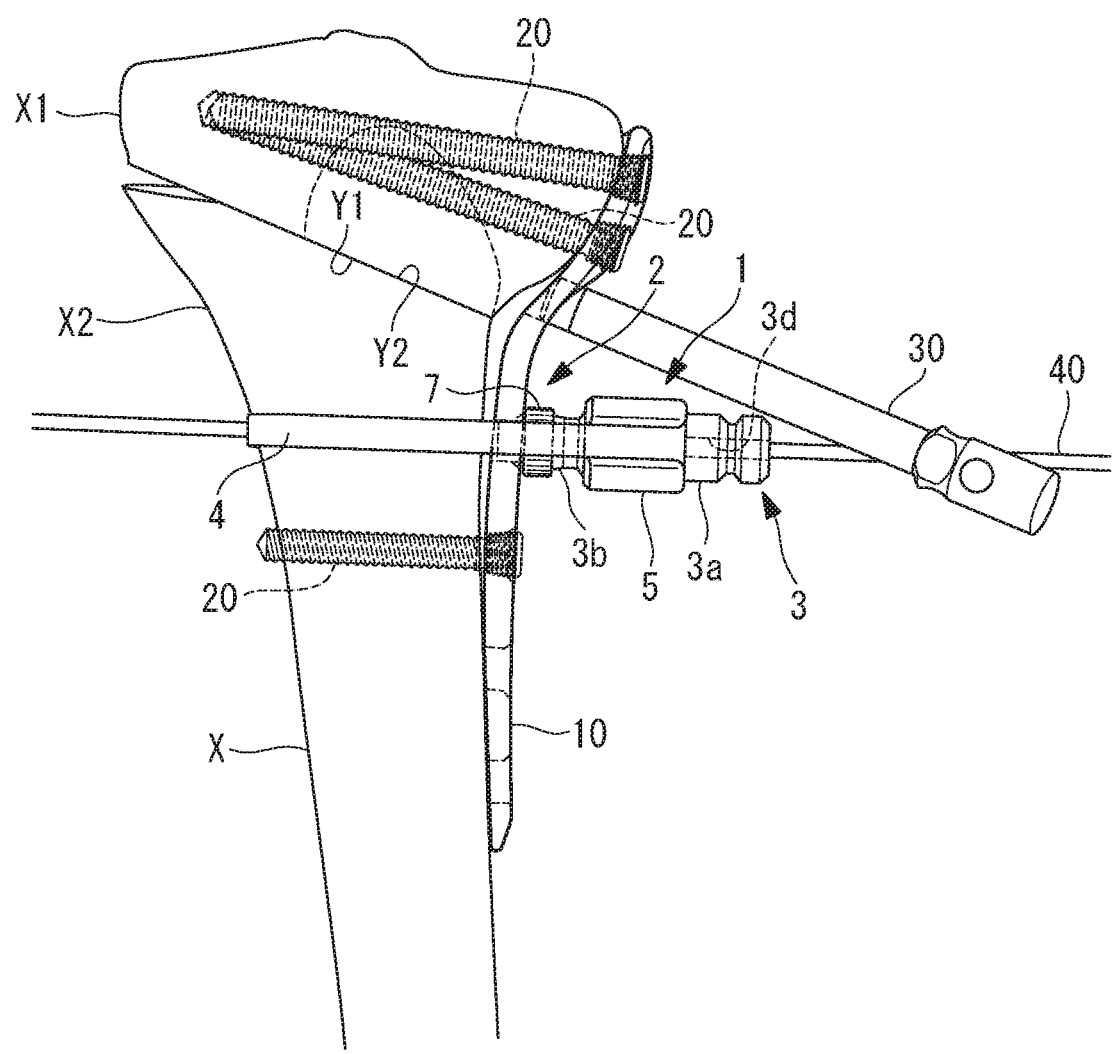
FIG. 7 is a diagram illustrating a method for using the modification of the pressing tool for bone surgery illustrated in FIG. 2 in combination with a guide pin.

In this embodiment, as illustrated in FIG. 7, a through hole 3d through which a guide pin 40 can pass may be formed in the pressing screw 3 so as to pass therethrough along the center axis of the shaft portion 3a so that the pressing tool 1 for bone surgery can be used in combination with the guide pin 40 of the screw 20. Considering the diameter of the guide pin 40 typically used in HTO, the diameter of the through hole 3d is preferably 2 mm or more.

In this manner, since the pressing screw 3 is guided along the guide pin 40 inserted into the through hole 3d, the position and the orientation of the pressing screw 3 with respect to the tibia X and the bone plate 10 can be stabilized.

Figure 8:
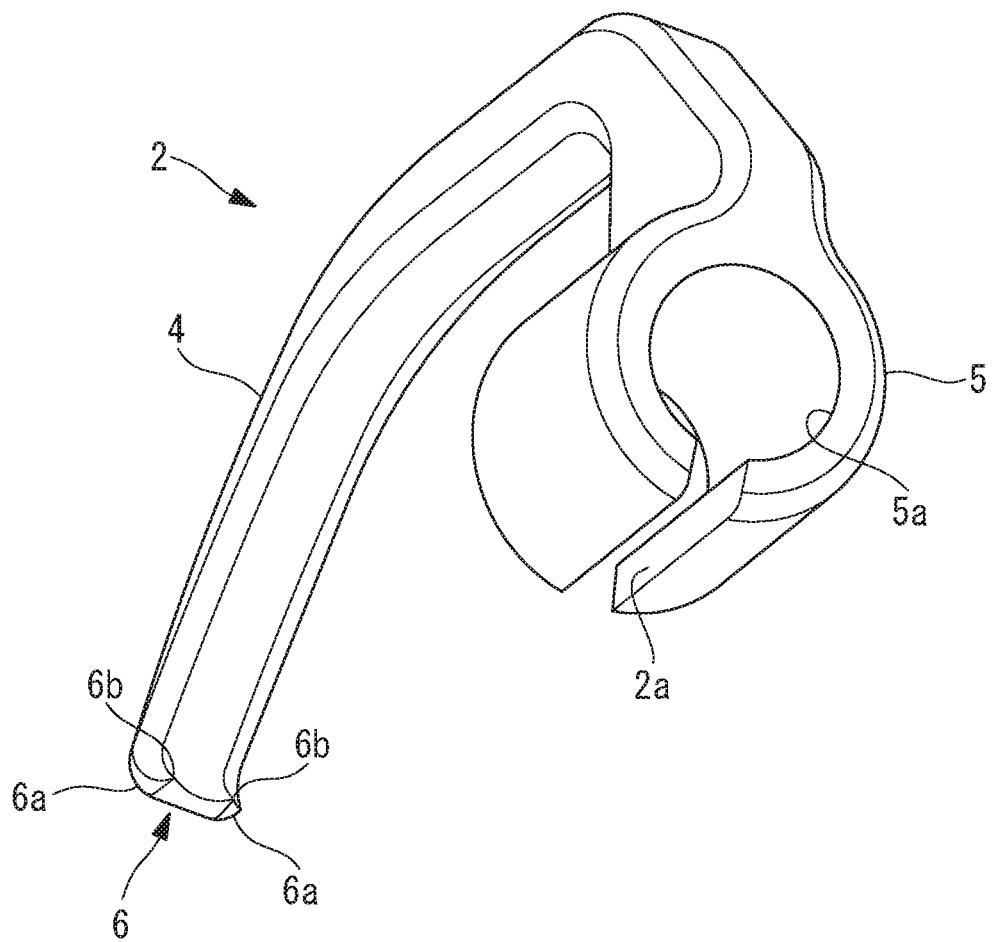
FIG. 8 is a perspective view of a modification of a hook member having a slit.

Furthermore, as illustrated in FIG. 8, a slit 2a for inserting and removing the guide pin 40 into and from inside the support portion 5 in the radial direction may be formed in the hook member 2. The slit 2a extends from the outer circumferential surface to the inner circumferential surface of the support portion 5 so that the interior of the screw hole 5a communicates with the exterior of the support portion 5, and is formed throughout the entire length in the longitudinal direction.

According to the hook member 2 having this slit 2a, after the guide pin 40 is inserted into the tibia X, the guide pin 40 is inserted into the support portion 5 through the slit 2a, and thus the hook member 2 can be easily installed with respect to the tibia X and the bone plate 10.

Figure 9:
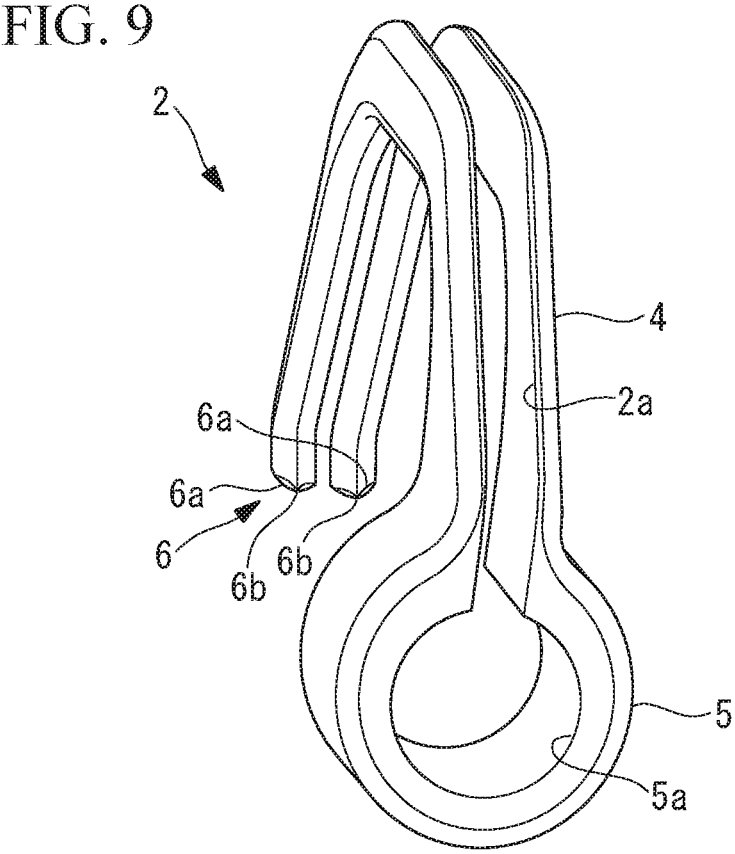
FIG. 9 is a perspective view of another modification of the hook member having a slit.

As illustrated in FIG. 9, the slit 2a may be formed so that the guide pin 40 is inserted into and removed from the screw hole 5a via the curved portion 4. In other words, the slit 2a may be formed throughout the entire length from the tip of the projection portion 6 to the screw hole 5a so as to halve the curved portion 4 and the projection portion 6.

In this embodiment, the head portion 3b of the pressing screw 3 is directly fitted into the screw hole 10a of the bone plate 10; alternatively, as illustrated in FIG. 7, a plug 7 that can be attached to the screw hole 10a and supports the head portion 3b may be further provided.

Figure 10:
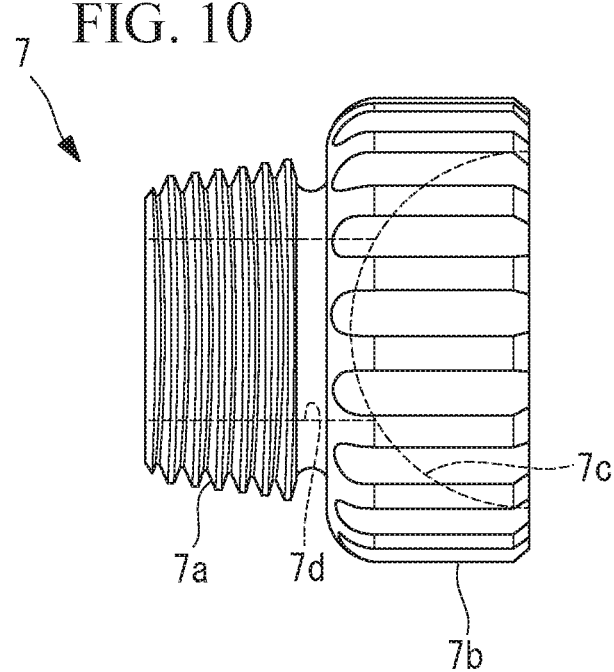
FIG. 10 is a side view of a plug installed in a modification of the pressing tool for bone surgery illustrated in FIG. 2.

As illustrated in FIG. 10, the plug 7 is equipped with a connecting portion 7a formed of a male thread that can be fastened to the screw hole 10a in the bone plate 10, and a receiving portion 7b that is disposed at one end of the connecting portion 7a and receives the head portion 3b. On the opposite side of the connecting portion 7a, the receiving portion 7b has a receiving surface 7c which is a concave and substantially spherical surface complementary to the substantially spherical pressing surface 3c of the head portion 3b and which supports the pressing surface 3c.

The compression force can be efficiently transmitted to the bone plate 10 from the pressing surface 3c of the head portion 3b via the receiving surface 7c by fitting the head portion 3b to the receiving surface 7c of the plug 7, the connecting portion 7a of which is attached to the screw hole 10a in the bone plate 10.

The solid angle of the receiving surface 7c is preferably 4 steradians or more and more preferably 2 π steradians or more. In this manner, the pressing surface 3c of the head portion 3b can be stably supported by the receiving surface 7c, and when the head portion 3b is rotated within the receiving surface 7c to adjust the direction of the compression force, displacement of the head portion 3b from the receiving surface 7c can be prevented.

The shape of the receiving surface 7c is not limited to the concave spherical surface, and may be any other shape externally tangential to the pressing surface 3c of the head portion 3b, for example, a polygonal shape.

To enable use of the plug 7 in combination with the guide pin 40, a through hole 7d through which a guide pin 40 can pass may be formed in the plug 7. The through hole 7d penetrates through the plug 7 along the center axis of the connecting portion 7a and opens at the center of the receiving surface 7c. The diameter of the through hole 7d is preferably 2 mm or more as with the diameter of the through hole 3d of the pressing screw 3.

In this manner, the screw hole 10a and the guide pin 40 passing through the through holes 7d and 3d can further stabilize the positions of the bone plate 10, the plug 7, and the pressing screw 3 relative to the tibia X.

Figure 11:
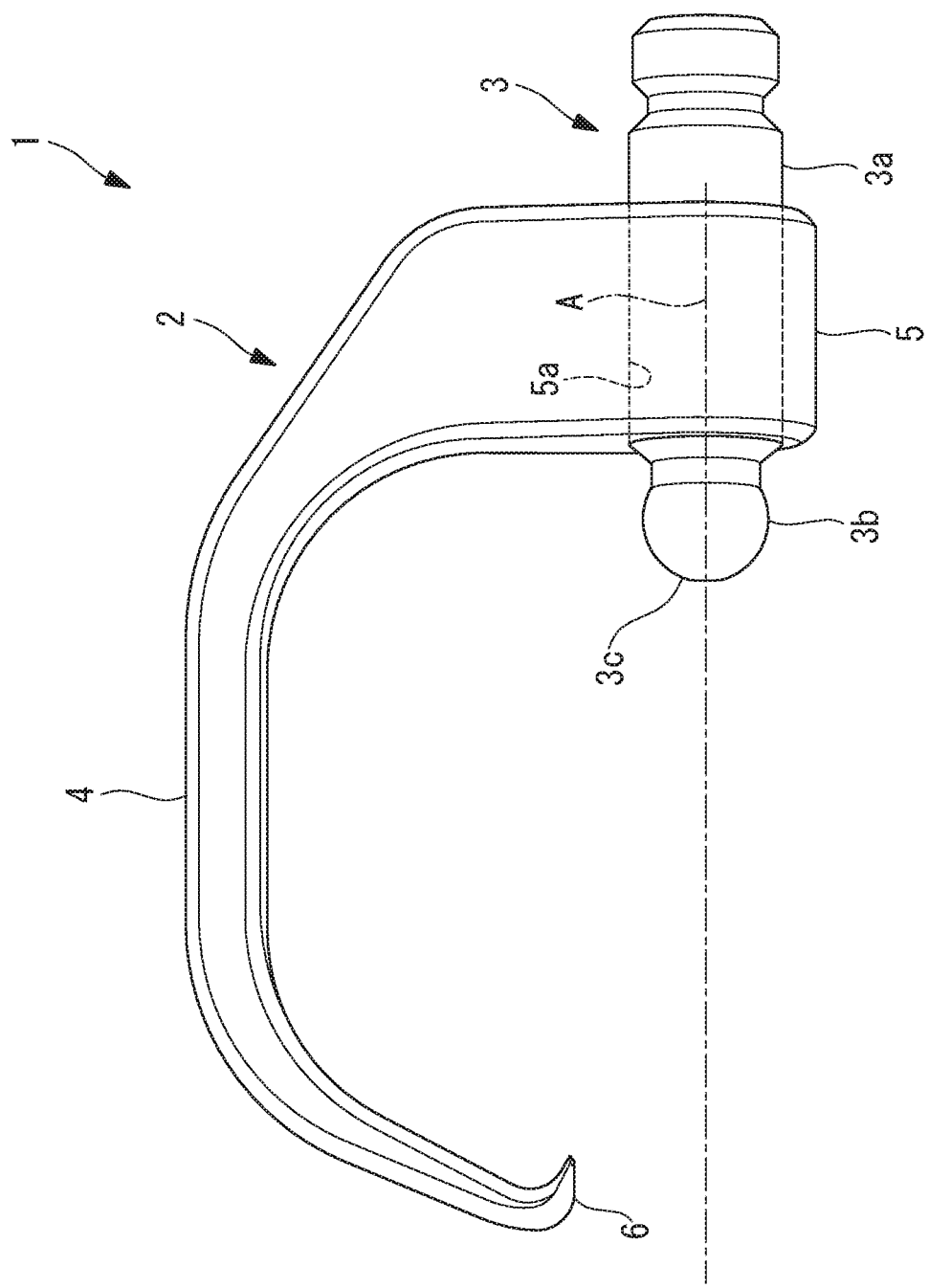
FIG. 11 is a side view of another modification of the hook member.

In this embodiment, the projection portion 6 is positioned on the extended line of the center axis A of the screw hole 5a; alternatively, as illustrated in FIG. 11, the position of the projection portion 6 may be offset from the extended line of the center axis A of the screw hole 5a in a direction intersecting the extended line.

In this case, a moment in a direction opposite to the offset direction of the projection portion 6 intersecting the center axis A of the screw hole 5a acts on the bone plate 10. Due to this moment, the bone plate 10 can also be moved in the bone plate 10 width direction with respect to the tibia X to adjust the position of the bone plate 10.

In this embodiment, physical power of the user is used as the driving force for advancing and retracting the pressing screw 3; alternatively, the pressing screw 3 may be moved by using oil pressure or water pressure, or by using an electric motor.

Figure 12:
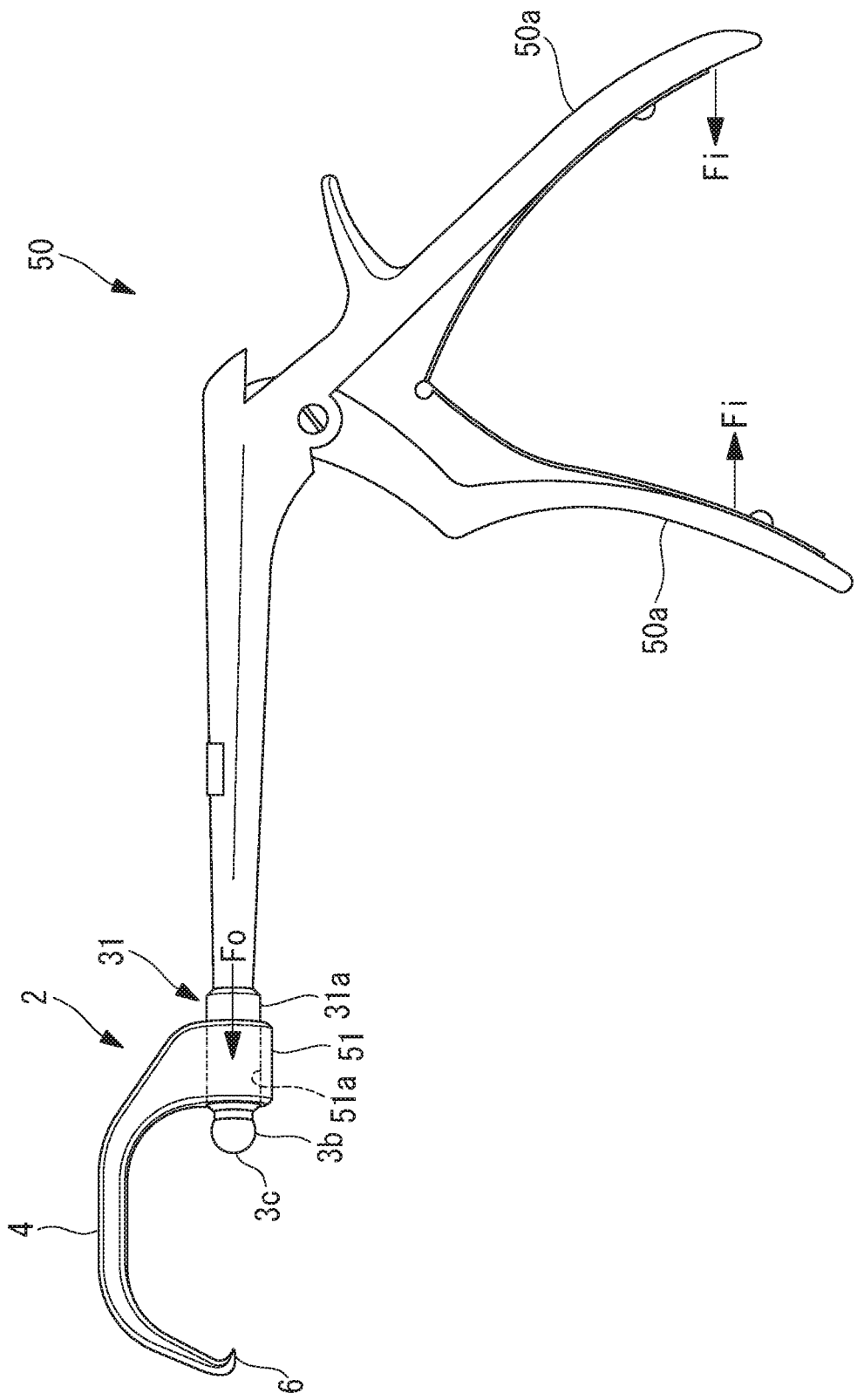
FIG. 12 is a diagram illustrating a modification of a pressing member and a pressing means.

Moreover, in this embodiment, the pressing screw 3 is used as the pressing member for pushing the bone plate 10 and generating a compression force; alternatively, a different pressing member may be used. For example, as illustrated in FIG. 12, a pressing member 31 may be equipped with a shaft portion 31a having a smooth side surface instead of the male thread 3a. In this case, a support portion 51 may have, instead of the screw hole 5a, a guide hole 51a which has a smooth inner surface and into which the shaft portion 31a of the pressing member fits so as to be movable in the longitudinal direction. The shaft portion 31a may be driven by using a tool that converts a particular motion of the user into a motion in the longitudinal direction of the shaft portion 31a.

For example, as illustrated in FIG. 12, a tool 50 that converts a rocking motion of a grip 50a that occurs when the user grasps the grip 50a, into a motion in the longitudinal direction of the shaft portion 31a may be used. The structure is preferably configured so that the following relationship is established between the force Fi the user applies to the grip 50a and the force Fo acting on the pressing member 31.

$$Fo = Fi \times \alpha (\alpha \geq 1)$$

In other words, the tool 50 is preferably configured to amplify the force Fi applied to the grip 50a and transmit the amplified force to the pressing member 31.

A mechanism that prevents return motion of the grip 50a may be provided to prevent unintended return motion of the grip 50a in the opposite direction. In this manner, it becomes possible to continuously and stably apply the compression force to the tibia X and the bone plate 10.

As a result, the following aspect is read from the above described embodiment of the present invention.

An aspect of the present invention provides a pressing tool for bone surgery, comprising: a pressurizing member formed substantially columnar shape having, at one end, a pressing surface formed of a convex and substantially spherical surface; and a hook member formed to have a hook shape that is to be engaged with a surface of a bone, the hook member having a support portion at a first end, the support portion is configured to support the pressing member so that the pressing surface is directed toward a second end, and a projection portion at the second end, the projection portion projecting toward the support portion and being to be bited into the surface of the bone, wherein the support portion supports the pressing member in state of the pressing member is moveable in a longitudinal direction toward the projection portion.

According to the aforementioned aspect of the present invention, after a bone joining member is placed on a surface of the bone in which an incision is made so as to bridge the incision, the hook member engages with the surface of the bone in such a manner that the bone and the bone joining member are sandwiched in the bone radial direction between the projection portion and the support portion at two ends of the hook member, and the projection portion is allowed to bite into the surface of the bone to fix the projection portion to the surface of the bone. The pressing member supported by the support portion is moved toward the projection portion in such a manner that the pressing surface presses the bone joining member toward the bone. As a result, a compression force in the bone radial direction is applied to the bone and the bone joining member sandwiched between the projection portion and the pressing member, and thus the bone and the bone joining member can make close contact with each other.

In this case, the direction in which the compression force is applied to the bone and the bone joining member is coincident with the direction in which the pressing member moves. Thus, when the hook member engages with the surface of the bone so that the longitudinal direction of the pressing member is inclined relative to the longitudinal axis direction of the bone, a compression force in both the bone radial direction and longitudinal axis direction is applied, and close contact can be achieved between the bone and the bone joining member and between the osteotomy surfaces of the bone.

Furthermore, in a state in which the hook member is engaged with the bone so that the pressing member is inclined with respect to the longitudinal axis direction of the bone, a large compression force can be stably applied to the bone and the bone joining member between the projection portion and the pressing member by fixing the projection portion at the second end of the hook member to the surface of the bone. In addition, since the pressing surface contacting the bone joining member is substantially spherical, the orientation of the hook member can be easily changed by rotating the pressing surface at the same position relative to the bone joining member and by shifting the projection portion in the longitudinal axis direction of the bone.

In the aspect described above, the pressing member may have a male thread and a head portion that is disposed at one end of the male thread and has the pressing surface, and the support portion may have a screw hole to be fastened to the male thread.

In this manner, since the rotation of the male thread inside the screw hole is converted into movement of the shaft portion in the longitudinal direction, it is easy to finely adjust the amount of the movement of the male thread to control the compression force applied to the bone and the bone joining member.

In the aspect described above, the projection portion may be at a position offset from an extended line of an axis line along which the pressing member is movable, in a direction intersecting the extended line.

In this manner, in addition to the pressing force in the longitudinal direction of the pressing member, a moment in a direction opposite to the offset direction of the projection portion intersecting the longitudinal direction of the pressing member can be applied to the bone joining member, and thus the bone joining member can be moved not only in a direction toward the bone but also in a direction opposite to the offset direction of the projection portion.

In the aspect described above, a distance between an extended line of an axis line along which the pressing member is movable and a middle portion of the hook member may be 15 mm or more and 35 mm or less.

In this manner, the size of the hook member becomes suitable for a large bone, such as the femur or the tibia.

In the aspect described above, the projection portion may have one or more pyramid-shaped projections having pointed ends.

In this manner, the pointed ends of the projections bite into the hard cortical bone covering the surface of the bone, and the projection portion can be easily fixed thereby.

In the aspect described above, the hook member may have a slit that allows an interior of the screw hole and an exterior of the support portion to communicate with each other in a radial direction of the screw hole and that extends in a direction along a center axis of the screw hole, wherein a guide pin is inserted into the screw hole in the radial direction.

In this manner, the hook member can be easily installed relative to the guide pin preliminarily inserted into the bone.

In the aspect described above, the pressing tool may further include a plug having a receiving portion having a concave receiving surface that is configured to support the pressing surface, and a connecting portion that is configured to connect the receiving portion to a bone joining member that is to be fixed to the surface of the bone.

In this manner, compared to the case in which the pressing surface is directly pressed against the bone joining member, the position of the pressing surface relative to the bone joining member can be stabilized by fitting the pressing surface to the receiving surface of the receiving portion of the plug connected to the bone joining member, and a pressing force can more efficiently be applied from the pressing surface to the bone joining member.

In the aspect described above, the plug may have a through hole that opens substantially at the center of the receiving surface and allows a guide pin to pass therethrough.

In this manner, the guide pin inserted into the bone passes through the bone joining member, the plug, and the pressing member, and thus, the positions of the bone joining member, the plug, and the pressing member relative to the bone can be stabilized. Considering the diameter of the guide pin typically used in osteotomy, the diameter of the through hole of the plug is preferably 2 mm or more.

In the aspect described above, the receiving surface of the receiving portion may have a solid angle of 4 steradians or more.

In this manner, the surface of the head portion opposite from the shaft portion can be more stably supported by the receiving surface, and a pressing force can be reliably applied from the pressing member to the bone joining member. The solid angle of the receiving surface is more preferably 2 π steradians or more so that no less than half of the outer surface of the head portion can be supported by the receiving surface.

REFERENCE SIGNS LIST 1 pressing tool for bone surgery
2 hook member
2a slit
3 pressing screw (pressing member)
3a shaft portion
3b head portion
3c pressing surface
3d through hole
4 curved portion
5 support portion
5a screw hole
6 projection portion
6a projection
6b pointed end
7 plug
7a connecting portion
7b receiving portion
7c receiving surface
7d through hole
10 bone plate (bone joining member)
10a screw hole
20 screw
30 drill sleeve
40 guide pin
A center line (axis line) of screw hole
X tibia
X1 higher portion
X2 lower portion
Y bone block removed portion
Y1, Y2 osteotomy surface

The invention claimed is:

1. A pressing tool for bone surgery, comprising:
a pressing member having a straight, columnar shaft portion extending along a longitudinal axis from a distal end to an opposite proximal end, said shaft portion having a male thread along the longitudinal axis and terminating in a head portion having a pressing surface formed of a convex and substantially spherical surface at said distal end; and
a hook member formed to have a hook shape that is to be engaged with a surface of a bone, the hook member having a cylindrical support portion at a first end, the support portion is configured to support the pressing member so that the pressing surface is directed toward a second end of the hook member, the hook member having at least one projection at the second end, the at least one projection projects toward the supporting portion and being configured to bite into a surface of the bone,
wherein the support portion supports the pressing member in state of the pressing member being movable in a longitudinal direction toward the at least one projection;
the cylindrical support portion has a screw hole extending therethrough in the longitudinal direction to be fastened to the male thread of the shaft portion;
the cylindrical support portion has a slit extending therethrough in a radial direction throughout an entire length of the cylindrical support portion in the longitudinal direction that allows an interior of the screw hole and an exterior of the support portion to communicate with each other in the radial direction of the screw hole, the slit extending in the longitudinal direction along a center axis of the screw hole, and a guide pin is inserted into the screw hole in the radial direction.

2. The pressing tool for bone surgery according to claim 1, wherein the at least one projection is positioned on an extended line of an axis line along which the pressing member is movable.

3. The pressing tool for bone surgery according to claim 1, wherein the at least one projection is at a position offset from an extended line of an axis line, along which the pressing member is movable, in a direction intersecting an extended line of an axis line along which the pressing member is movable.

4. The pressing tool for bone surgery according to claim 1, wherein a distance between an extended line of an axis line along which the pressing member is movable and a middle portion of the hook member is 15 mm or more and 35 mm or less.

5. The pressing tool for bone surgery according to claim 1, wherein the at least one projection has one or more pyramid-shaped projections having pointed ends.

6. The pressing tool for bone surgery according to claim 1, further comprising a plug having a receiving portion having a concave receiving surface that is configured to support the pressing surface, and a connecting portion that is configured to connect the receiving portion to a bone joining member that is to be fixed to the surface of the bone.

7. The pressing tool for bone surgery according to claim 6, wherein the plug has a through hole that opens substantially at the center of the receiving surface and allows a guide pin to pass therethrough.

8. The pressing tool for bone surgery according to claim 6, wherein the receiving surface of the receiving portion has a solid angle of 4 steradians or more.

* * * * *